US009668773B2

(12) United States Patent
Alexander et al.

(10) Patent No.: US 9,668,773 B2
(45) Date of Patent: Jun. 6, 2017

(54) SPINAL IMPLANT FOR USE IN THORACIC INSUFFICIENCY SYNDROME

(71) Applicant: GLOBUS MEDICAL, INC, Audubon, PA (US)

(72) Inventors: Victoria Alexander, Royersford, PA (US); Alexander Artaki, Philadelphia, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 35 days.

(21) Appl. No.: 14/212,293

(22) Filed: Mar. 14, 2014

(65) Prior Publication Data
US 2014/0277147 A1 Sep. 18, 2014

Related U.S. Application Data

(60) Provisional application No. 61/782,835, filed on Mar. 14, 2013.

(51) Int. Cl.
*A61B 17/88* (2006.01)
*A61B 17/70* (2006.01)

(52) U.S. Cl.
CPC ........ *A61B 17/7014* (2013.01); *A61B 17/707* (2013.01); *A61B 17/7055* (2013.01); *A61B 17/7071* (2013.01)

(58) Field of Classification Search
CPC ............ A61B 17/7068; A61B 17/7064; A61B 17/7049; A61B 17/7062; A61B 17/7065; A61B 17/7067; A61B 17/7002; A61B 17/7047; A61B 17/7076; A61B 17/025; A61B 17/7014; A61B 17/7052; A61B 2017/681; A61B 17/707; A61B 17/7071; A61B 17/7056
USPC .................................. 606/246–279
See application file for complete search history.

(56) References Cited

U.S. PATENT DOCUMENTS

| | | | | |
|---|---|---|---|---|
| 6,051,007 A | * | 4/2000 | Hogendijk et al. | ........... 606/151 |
| 6,432,108 B1 | * | 8/2002 | Burgess et al. | ................ 606/252 |
| 2008/0086115 A1 | * | 4/2008 | Stoklund | ............ A61B 17/8076 606/1 |
| 2008/0147125 A1 | * | 6/2008 | Colleran et al. | .............. 606/280 |
| 2010/0057127 A1 | * | 3/2010 | McGuire et al. | ............. 606/246 |
| 2010/0121381 A1 | * | 5/2010 | Berta | ................. A61B 17/7055 606/264 |
| 2011/0087286 A1 | * | 4/2011 | Ciupik et al. | ................. 606/249 |
| 2011/0224731 A1 | * | 9/2011 | Smisson et al. | .............. 606/249 |
| 2011/0238114 A1 | * | 9/2011 | Lim | ................... A61B 17/7065 606/248 |

* cited by examiner

*Primary Examiner* — Eduardo C Robert
*Assistant Examiner* — Tara R Carter

(57) ABSTRACT

An implant system for correcting deformities is provided. The implant system includes A proximal extension having a hollow interior and a distal extension configured to be received within the hollow interior of the proximal extension. The implant system also includes a locking element configured to lock the distal extension from moving with respect to the proximal extension. The distal extension is configured with ratchet teeth on a top surface for interacting with a distractor instrument for contacting or distracting the distal extension with respect to the proximal extension. The proximal extension and distal extension are configured to receive clamping elements for coupling to the implant to anatomical regions of the body.

17 Claims, 8 Drawing Sheets

SPINAL IMPLANT FOR USE IN THORACIC INSUFFICIENCY SYNDROME

CROSS-REFERENCE TO RELATED APPLICATIONS

This application is a non-provisional application which claims priority to Provisional Application Ser. No. 61/782,835 filed on Mar. 14, 2013, which is incorporated in its entirety herein.

FIELD OF THE INVENTION

The present invention is related to an implant for the treatment of deformities and trauma in the spine.

BACKGROUND OF THE INVENTION

Anatomic boundaries of the thorax limit the growth of the lungs. The thorax consists of the spine, the chondral and osseous ribs, and the sternum. Normally the spine and the ribs work together as a dynamic biomechanical structure to work efficiently at respiration. When a significant deformity of the thoracic cage exists, it changes the dynamics of this system, and can interfere with normal respirations and lung development. Thoracic Insufficiency Syndrome (TIS) is the inability of the thorax to support normal respiration or lung growth. TIS can occur in patients with congenital, infantile or neuromuscular scoliosis, congenital anomalies of the ribs, acquired chest wall deformities, and skeletal dysplasias. Malformations of the chest, spine or ribs can result in decreased thoracic volume and inadequate lung development or thoracic stiffness and lack of compliance.

There is no standard treatment for TIS associated with thoracic spine and rib cage deformity. Goals of treatment include optimizing conditions for growth and function of the thorax and lungs, maximizing spine length and minimizing spine deformity. Recently, one treatment option for patients with congenital scoliosis and fused ribs has been to perform an opening wedge thoracostomy operation with implantation in order to maintain expansion of the constricted hemithorax. Implants are then expanded every 4 to 6 months depending on growth rate. The implants currently available for this procedure have issues with migration, implant prominence, soft tissue breakdown, and infection.

SUMMARY OF THE INVENTION

An implant system for correcting deformities is provided. The implant system includes A proximal extension having a hollow interior and a distal extension configured to be received within the hollow interior of the proximal extension. The implant system also includes a locking element configured to lock the distal extension from moving with respect to the proximal extension. The distal extension is configured with ratchet teeth on a top surface for interacting with a distractor instrument for contacting or distracting the distal extension with respect to the proximal extension. The proximal extension and distal extension are configured to receive clamping elements for coupling to the implant to anatomical regions of the body.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE DRAWINGS

Figure 1:
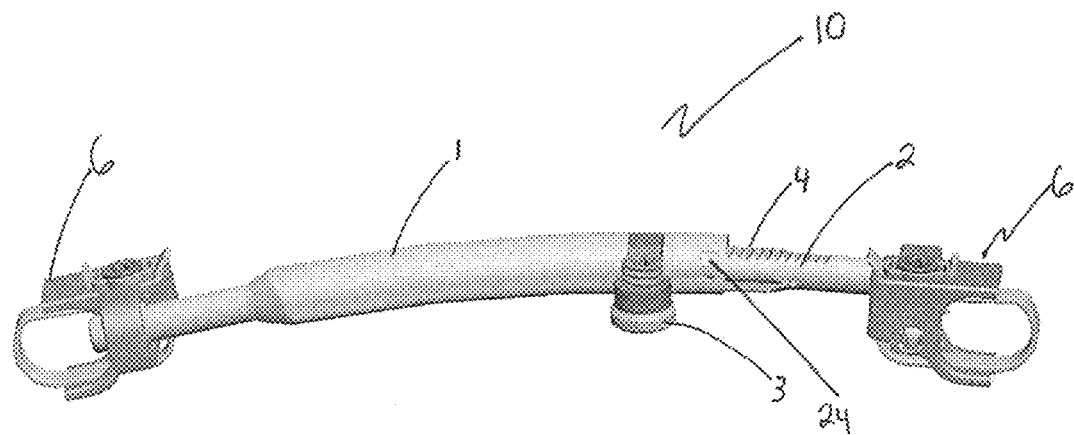
FIG. 1 illustrates the TIS implant system according to a preferred embodiment of the invention.
Figure 2:
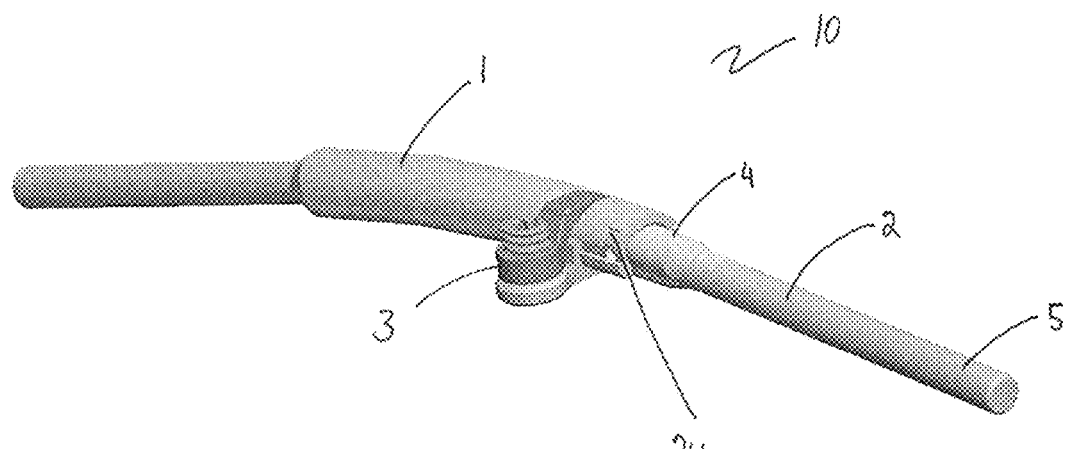
FIG. 2 illustrates the central components of the TIS implant system according to a preferred embodiment of the invention.

The TIS implant system 10 consists of a series of extension members with outgoing rods that can connect to hooks for connections from rib to rib, rib to spine, and rib to iliac. The components come in varying sizes and are modular so that they can be assembled in a variety of ways to best suit the individual patient.

The system 10 is comprised of a proximal extension (1) and a distal extension (2) which slide within one another and can be locked together with the locking feature (3) that utilizes a hex instrument to turn the set screw and lock. The distal extension has teeth (4) on the top surface which interact with the distractor instrument which is described in more detail below.

Figure 3:
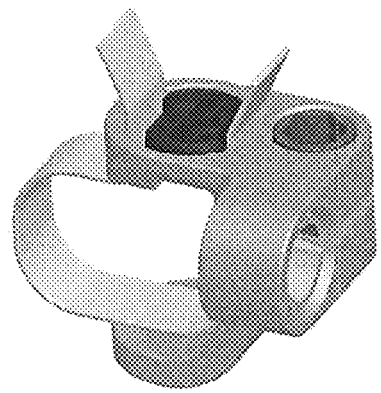
FIGS. 3-5 illustrate a more detailed view of the clamping element used in the system shown in FIG. 1.
Figure 4:
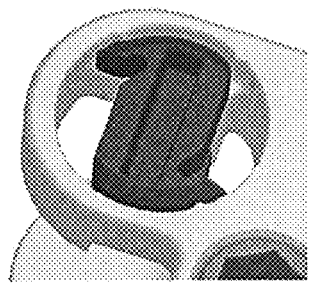
Figure 5:
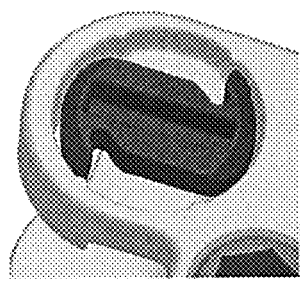
Figure 6:
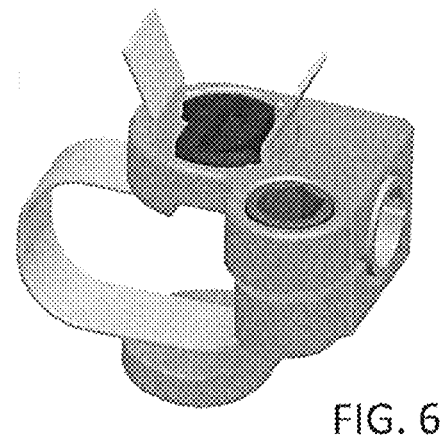
FIGS. 6-8 illustrates an alternative clamping element for use with the TIS implant system.
Figure 7:
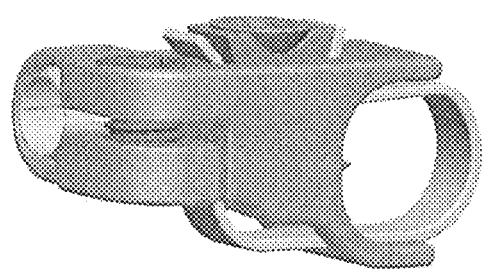
Figure 8:
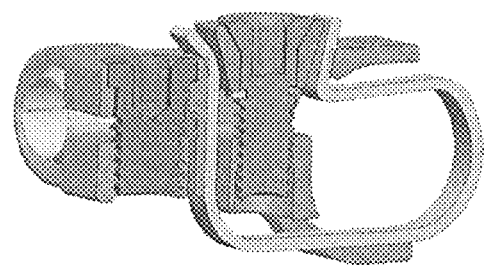

Each extension member has an outgoing rod (5) which can be used to connect to other attachment members. The extension members will be made with several radii and length options. The rib hook (6) can be attached at the proximal and distal ends on the outgoing rod in order to fix the construct to the ribs. Several iterations of the rib hook are shown. One design as shown in FIGS. 3-5 uses a cam mechanism to lock the PET band to the hook. This design has an offset hole which captures the rod and a set screw clamps the bushing to lock onto the outgoing rod. Another design as shown in FIG. 6 also uses a cam mechanism to lock the PET band to the hook. This design has a hole which is inline with the implant that captures the rod and a set screw clamps the bushing to lock onto the outgoing rod. A third hook design FIGS. 7 and 8 utilizes a set screw with a wedge to lock down on the PET band. This design would have an offset connection to the outgoing rod which is locked with a set screw that clamps a bushing.

Figure 9:
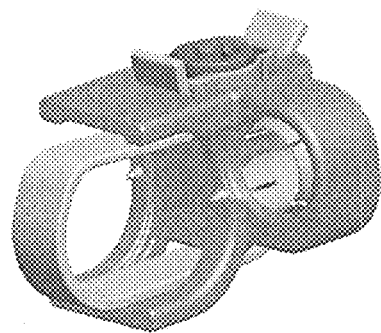
FIGS. 9 and 10 illustrate yet another alternative clamping element used with TIS implant system.
Figure 10:
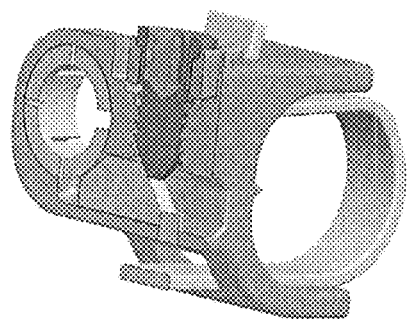
Figure 11:
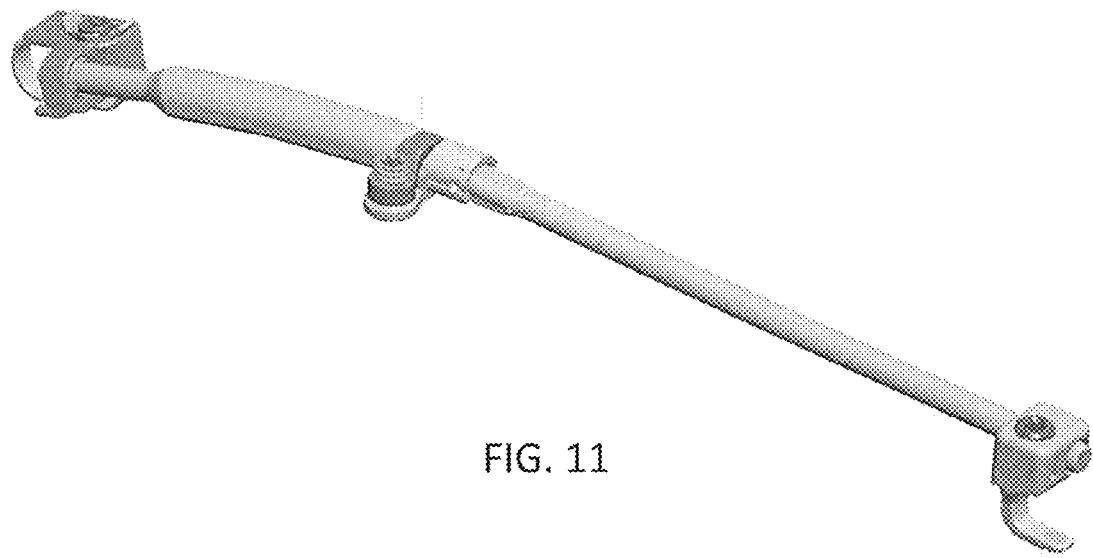
FIG. 11 illustrates an embodiment of the TIS implant system using a two different types of clamping elements.
Figure 12:
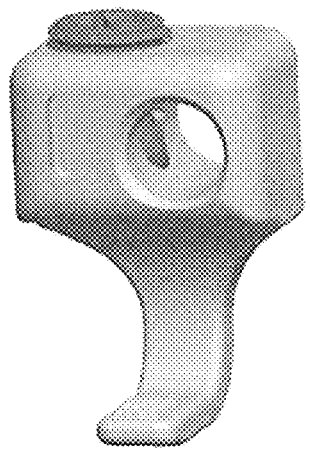
FIGS. 12 and 13 illustrate a hook type clamping element for use with the TIS implant system illustrated in either FIG. 1 or FIG. 11.
Figure 13:
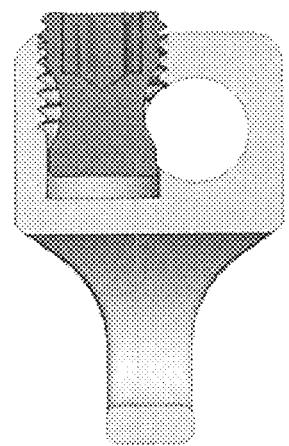

The final design FIGS. 9 and 10 consists of a combination cam and set screw design, when the cam is turned it provisionally locks the PET band to the hook. Then the set screw is rotated to lock the PET band and to also push a pin which will clamp the bushing to lock the hook to the outgoing rod. In all designs, a PET band threads through the hook and wraps around the rib to securely attach the hook to the rib. In an alternative embodiments, closed lamina hooks as shown in FIGS. 11, 12, and 13 can be used to connect the outgoing rod to the lumbar lamina for a rib to spine construct. The closed design allows for a lower profile. S-hooks can also be used to connect the outgoing rod to the iliac crest for a rib to iliac constructs. This style simply hooks over the iliac wing and allows for distraction.

Figure 14:
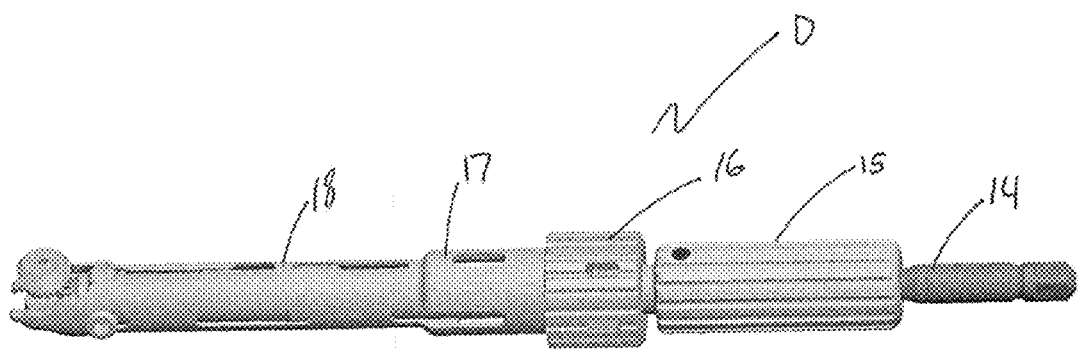
FIGS. 14 and 15 illustrate a distractor instrument used in manipulating the TIS implant system.
Figure 15:
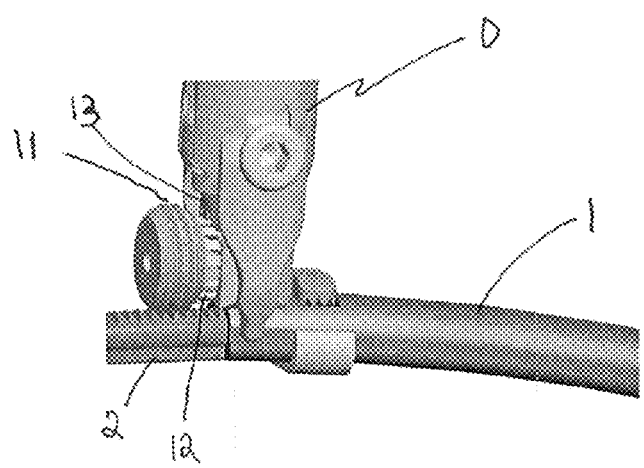

Now, turning to FIGS. 14 and 15, the distractor instrument according to the present invention is shown. The main purpose of the distractor instrument (D) is to distract the extension member during the initial implantation of the device and any subsequent expansion procedures. It performs the distraction by sliding the proximal extension (1) and the distal extension (2) apart such that the extension member increases in length. It also has the ability to contract the extension member (EM) should the surgeon wish to do so. The distractor instrument achieves distraction by utilizing a worm gear mechanism as more clearly illustrated in FIG. 15. The Worm (11) of the distractor instrument engages with the teeth of the distal extension (2), and depending on its direction of rotation, 2 will either "exit" or further "enter" 1. The worm gear 11 rotates by virtue of a bevel gear train. The worm gear 11 is positively locked to the First Gear (12), which engages with the Second Gear (13). The second gear 13 is connected to the Central Shaft (13). By turning the Central Shaft 14, either directly or through an attachment handle, the surgeon drives the gear train to drive the Worm. The Counter Torque (15) serves as a natural handle for the instrument and, as its name implies, it counters the torque that the surgeon delivers through the instrument via central shaft 14.

Figure 16:
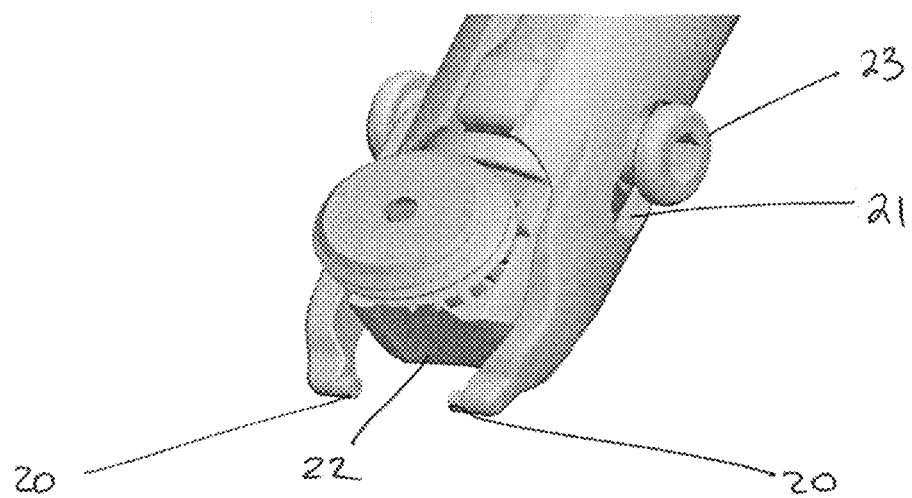
FIG. 16 illustrates the distal end of the distractor instrument.
Figure 17:
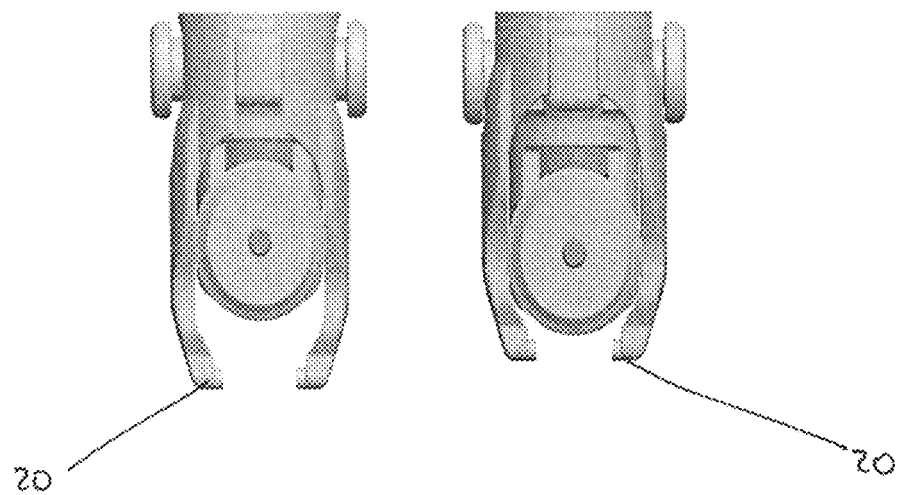
FIG. 17 illustrates the distractor instrument in an open position and a closed position.
Figure 18:
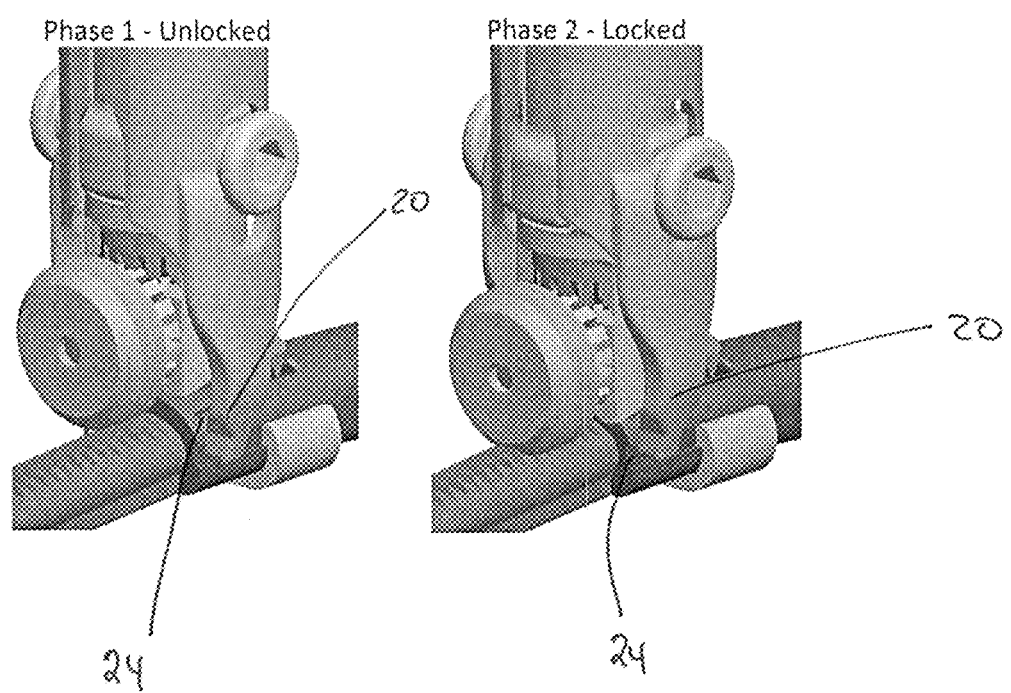
FIG. 18 illustrates the distractor instrument coupled to the implant system in an open position and a closed position.

FIGS. 16-18 illustrate the distal end of the distractor instrument in more detail. The purpose of the lock knob (16) is configured to engage the distractor instrument with the extension member, and after expansion, to disengage. Turning the lock knob slides 16 the clamp (17) along the main body (18). Clockwise rotation slides the clamp such that its engagement tabs 20 as shown move closer to the base (22) of the main body, while counterclockwise does the opposite. The Clamp Alignment Slots (21) and Clamp Alignment Knobs (23) limit the travel between clamp and the main body of the instrument and maintain their alignment with respect to each other.

Now turning to FIG. 18, the engagement between the distractor instrument and the extension member occurs in three phases. During Phase 1 the distractor instrument is positioned on the implant in an unlocked position. The clamp 17 is positioned relative to the main body 18 such that engagement tabs 20 can splay apart. Once the distractor instrument is an unlocked position, it is positioned on the implant. The engagement tabs 10 are then aligned with the extension member engagement slots (24) and "snaps" the inward protrusions of the distractor instrument into the recesses of 24. After initial engagement is made, the distractor instrument is moved to Phase 2 by rotating the lock knob clockwise until base 22 meets the topmost surface of proximal extension 1.

At this point, the implant is fully engaged with the teeth 2 of the extension member which can be either distracted or compressed. To disengage the distractor instrument from the extension member, the lock knob is turned counterclockwise back through Phase 1 and on to Phase 3. Phase 3, the disengagement phase, is achieved when knob 23 is moved into the upper portion of the slot 21. During this travel, a splaying feature splays apart such that the inward protrusions clear the recesses of the extension member and the distractor instrument can be lifted from the extension member.

The invention allows for treatment of Thoracic Insufficiency Syndrome. The system is designed to address shortcomings with the current TIS systems. With the use of the PET band the implants are able to be lower profile to prevent implant prominence and they are more securely attached to the rib which could prevent migration of the implants. The extension member locking mechanism utilizing the teeth feature allows for distraction in smaller increments than the competitive products. Furthermore, the simple distractor instrument allows for a smaller incision for routine implant distractions.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

We claim:

1. An implant system for correcting deformities comprising:
    a proximal extension having a hollow interior, wherein the proximal extension is attached to a first rib hook;
    a distal extension configured to be received within the hollow interior of the proximal extension, wherein the distal extension is attached to a second rib hook, wherein at least one of the first and second rib hooks includes a band threaded through the rib hook such that the band is configured to wrap around a rib to securely attach the rib hook to the rib, wherein a set screw locks down on the band to secure the band in the first or second rib hook;
    a locking element configured to lock the distal extension from moving with respect to the proximal extension;
    wherein the distal extension is configured with ratchet teeth on a top surface for interacting with a distractor instrument for contacting or distracting the distal extension with respect to the proximal extension.

2. The implant system of claim 1, wherein the first rib hook includes a first loop and the second rib hook includes a second loop.

3. The implant system of claim 2, wherein at least one of the first rib hook and the second rib hook comprises a cam mechanism.

4. The implant system of claim 1, wherein the band comprises PET.

5. The implant system of claim 1, wherein the distractor instrument comprises a worm gear.

6. The implant system of claim 5, wherein the worm gear is capable of rotation via a bevel gear train.

7. The implant system of claim 1, wherein the distractor instrument comprises a lock knob.

8. The implant system of claim 1, wherein at least one the first and second rib hooks are c-shaped having a first end and a second end, and the band extends from the first end of the rib hook and loops around to the second end of the rib hook.

9. The implant system of claim 1, wherein the band extends from a first end to a second end, and a first portion of the band proximate to the first end is positioned on one side of the set screw and a second portion of the band proximate to the second end is positioned on another side of the set screw.

10. The implant system of claim 1, wherein the proximal extension is substantially cylindrical.

11. The implant system of claim 1, wherein at least one of the first and second rib hooks and the band forms a closed loop and an inner diameter of the closed loop is adjustable in size.

12. An implant system for correcting deformities comprising:
   a proximal extension having a hollow interior;
   a distal extension configured to be received within the hollow interior of the proximal extension, wherein at least one of the proximal extension and the distal extension is attached to a rib hook, wherein the rib hook includes a band threaded through the rib hook such that the band is configured to wrap around a rib to securely attach the rib hook to the rib, wherein a set screw locks down on the band to secure the band in the first or second rib hook;
   a locking element configured to lock the distal extension from moving with respect to the proximal extension;
   wherein the distal extension is configured with ratchet teeth on a top surface for interacting with a distractor instrument for distracting the distal extension with respect to the proximal extension.

13. The implant system of claim 12, wherein the rib hook comprises a loop.

14. The implant system of claim 12, wherein the band comprises PET.

15. The implant system of claim 12, wherein the rib hook comprises an offset connection to receive a rod member therein.

16. The implant system of claim 12, wherein the distractor instrument comprises a worm gear.

17. The implant system of claim 16, wherein the worm gear is capable of rotation via a bevel gear train.

* * * * *